(12) United States Patent
Sullivan et al.

(10) Patent No.: US 10,524,699 B2
(45) Date of Patent: Jan. 7, 2020

(54) METHOD AND SYSTEM FOR MONITORING TERRAIN AND GAIT AND PREDICTING UPCOMING TERRAIN

(71) Applicants: Christopher Sullivan, Rochester, NY (US); Elizabeth DeBartolo, Pittsford, NY (US); Kathleen Lamkin-Kennard, Hamlin, NY (US)

(72) Inventors: Christopher Sullivan, Rochester, NY (US); Elizabeth DeBartolo, Pittsford, NY (US); Kathleen Lamkin-Kennard, Hamlin, NY (US)

(73) Assignee: ROCHESTER INSTITUTE OF TECHNOLOGY, Rochester, NY (US)

( * ) Notice: Subject to any disclaimer, the term of this patent is extended or adjusted under 35 U.S.C. 154(b) by 542 days.

(21) Appl. No.: 14/136,567

(22) Filed: Dec. 20, 2013

(65) Prior Publication Data

US 2014/0180173 A1   Jun. 26, 2014

Related U.S. Application Data

(60) Provisional application No. 61/745,883, filed on Dec. 26, 2012.

(51) Int. Cl.
*A61B 5/11* (2006.01)
*A61B 5/00* (2006.01)

(52) U.S. Cl.
CPC ............ *A61B 5/112* (2013.01); *A61B 5/0002* (2013.01)

(58) Field of Classification Search
CPC ......... A61F 2/68; A61F 2/6607; A61B 5/1038
See application file for complete search history.

(56) References Cited

U.S. PATENT DOCUMENTS

| | | | |
|---|---|---|---|
| 5,186,062 A | 2/1993 | Roost | |
| 6,360,597 B1 | 3/2002 | Hubbard, Jr. | |
| 7,499,775 B2 | 3/2009 | Filippov et al. | |
| 7,531,006 B2 | 5/2009 | Clausen et al. | |
| 7,637,957 B2 | 12/2009 | Ragnarsdottir et al. | |
| 7,650,204 B2 | 1/2010 | Dariush | |
| 2005/0070834 A1* | 3/2005 | Herr | A61B 5/1038 602/28 |
| 2007/0050047 A1* | 3/2007 | Ragnarsdottlr | A61F 2/68 623/24 |
| 2008/0053253 A1 | 3/2008 | Moore et al. | |
| 2008/0108913 A1 | 5/2008 | Lengsfeld et al. | |
| 2010/0174385 A1 | 7/2010 | Casler et al. | |
| 2011/0060478 A1 | 3/2011 | Nicholaou | |
| 2011/0112447 A1 | 5/2011 | Hsiao-Wecksler et al. | |
| 2011/0218463 A1 | 9/2011 | Hodgins et al. | |
| 2012/0016493 A1 | 1/2012 | Hansen et al. | |
| 2012/0136459 A1 | 5/2012 | Herr et al. | |
| 2012/0232672 A1 | 9/2012 | Ragnardottir et al. | |

FOREIGN PATENT DOCUMENTS

WO      2012007855      1/2012

\* cited by examiner

*Primary Examiner* — Patrick Fernandes
(74) *Attorney, Agent, or Firm* — Bond, Schoeneck & King, PLLC; Joseph Noto

(57) ABSTRACT

The system and method of the present invention utilizes one or more sensors to generate data attached to a person interfaced with a data monitoring computing device and a data management computing device monitoring the terrain the individual is traversing and gait at which the individual is traversing the terrain, in addition to predicting the terrain the individual is about to traverse.

36 Claims, 17 Drawing Sheets

METHOD AND SYSTEM FOR MONITORING TERRAIN AND GAIT AND PREDICTING UPCOMING TERRAIN

CROSS REFERENCE

This application claims the benefit of U.S. Provisional Patent Application Ser. No. 61/745,883, filed Dec. 26, 2012, the contents of which are hereby incorporated by reference in its entirety.

This invention was made with government support under grant number BES-0527358 awarded by National Science Foundation. The government has certain rights in the invention.

FIELD

This invention relates to a method and system for monitoring terrain and gait and predicting upcoming terrain.

BACKGROUND

An Ankle Foot Orthotic (AFO) has been around for centuries and was created to substitute functionality of an ankle that had been lost to injury or disease. A common reason a person might be prescribed an AFO is a condition called foot-drop which is characterized by the inability to raise and/or lower the foot. Foot-drop can be caused nerve injury, neurological disorders, or muscular disorders. This incapacitation of the person's foot leads to unnatural gait and joint fatigue, as well as increasing the person's likelihood of tripping and becoming seriously injured. Hard plastic AFOs that hold a person's foot in a neutral position are the current standard for treating foot-drop. These AFOs can come in many different shapes and sizes which illustrate the wide variety in functionality of someone with foot-drop.

Unfortunately, the restrictive nature of the AFO can cause unnatural movements in the person's foot. These unnatural movements are more exaggerated when walking down stairs and ramps, as the natural thing to do is to land toe first, the opposite of what the AFO allows the person to do.

The most common existing manners of tracking human gait patterns and/or controlling active AFOs are stationary (clinic-based) optical or force-plate systems, inertial motion units (IMUs) that include accelerometers and/or gyroscopes, or force sensors that detect foot contact with the ground. External optical systems and force plates are strictly for in-clinic use, as they are static systems that cannot move with the user. IMUs can require significant additional signal processing to compensate for gyroscope drift or differentiation or integration of acceleration data. Those IMUs that also include magnetometers are susceptible to interference from external magnetic fields. Force sensors are limited to detecting ground contact and do not give other information specific to leg position or terrain/intensity level.

As far as gait tracking has been concerned, the general trend in gait tracking devices has been to increase the accuracy of the devices. Most modern gait tracking is achieved with the use of video systems that track markers attached to people. While increased accuracy is an important improvement, simpler, low-cost ways to measure the change in a person's gait over time are equally important.

Meanwhile, previously terrain detection has been purely a study for robotics. As a result, the techniques used for a non-robotic application have yet to be fully investigated. In the field of rehabilitation, orthotics, and prosthetics, terrain detection has been limited to characterizing the ground that the foot has already contacted, rather than predicting the ground that is approaching.

SUMMARY

In accordance with an aspect of the present invention there is provided a method for monitoring terrain and gait of a subject traversing terrain, the method including: receiving by a management computing device first distance data between a first terrain sensor attached to a first appendage of the subject and approaching terrain throughout a gait cycle of the subject while traversing the terrain; receiving by the management computing device first gait speed data relating to the gait of the subject from a first gait sensor on the first appendage of the subject throughout the gait cycle of the subject while traversing the terrain; and providing by the management computing device the received first gait speed data and the first distance data for the subject.

In accordance with another aspect of the present invention there is provided a non-transitory computer readable medium having stored thereon instructions for simultaneously monitoring terrain and gait of a subject traversing terrain comprising machine executable code which when executed by at least one processor, causes the processor to perform steps including: receiving by a management computing device first distance data between a first terrain sensor attached to a first appendage of the subject and approaching terrain throughout a gait cycle of the subject while traversing the terrain; receiving by the management computing device first gait speed data relating to the gait of the subject from a first gait sensor on the first appendage of the subject throughout the gait cycle of the subject while traversing the terrain; and providing by the management computing device the received first gait speed data and the first distance data for the subject.

In accordance with another aspect of the present invention there is provided a terrain and gait monitoring system including: one or more sensors; and a management computing device coupled to the one or more sensors, the management computing device comprising a memory coupled to one or more processors which are configured to execute programmed instructions stored in the memory including: receiving first distance data between a first terrain sensor attached to a first appendage of the subject and approaching terrain throughout a gait cycle of the subject while traversing the terrain; receiving first gait speed data relating to the gait of the subject from a first gait sensor on the first appendage of the subject throughout the gait cycle of the subject while traversing the terrain; and providing the received first gait speed data and the first distance data for the subject.

DETAILED DESCRIPTION

A user-centered proximity measurement system designed to capture integrated data on gait and terrain while traversing terrain is disclosed. The system can be used to monitor gait and terrain, identify terrain traversed, and predict upcoming terrain about to be traversed. Optical sensor(s) are employed to measure terrain while the terrain is being traversed. The sensor(s) measures the distance from the sensor to a point on the ground ahead of the user throughout the gait cycle. The period of the gait cycle or speed at which the user is traversing the terrain can be derived from the terrain data or from a sensor generating high/low data in the gait cycle. This data can be used to calibrate the system to an individual user and construct models of a user's gait pattern over different terrain types. After calibration, the type of terrain traversed can be determined by comparing the new data generated to the terrain models. The data generated through a portion of the gait cycle can be used to predict the type of upcoming terrain. The present system offers long-term gait monitoring and the ability to distinguish between subtly different terrain types based on ground profile.

Figure 1:
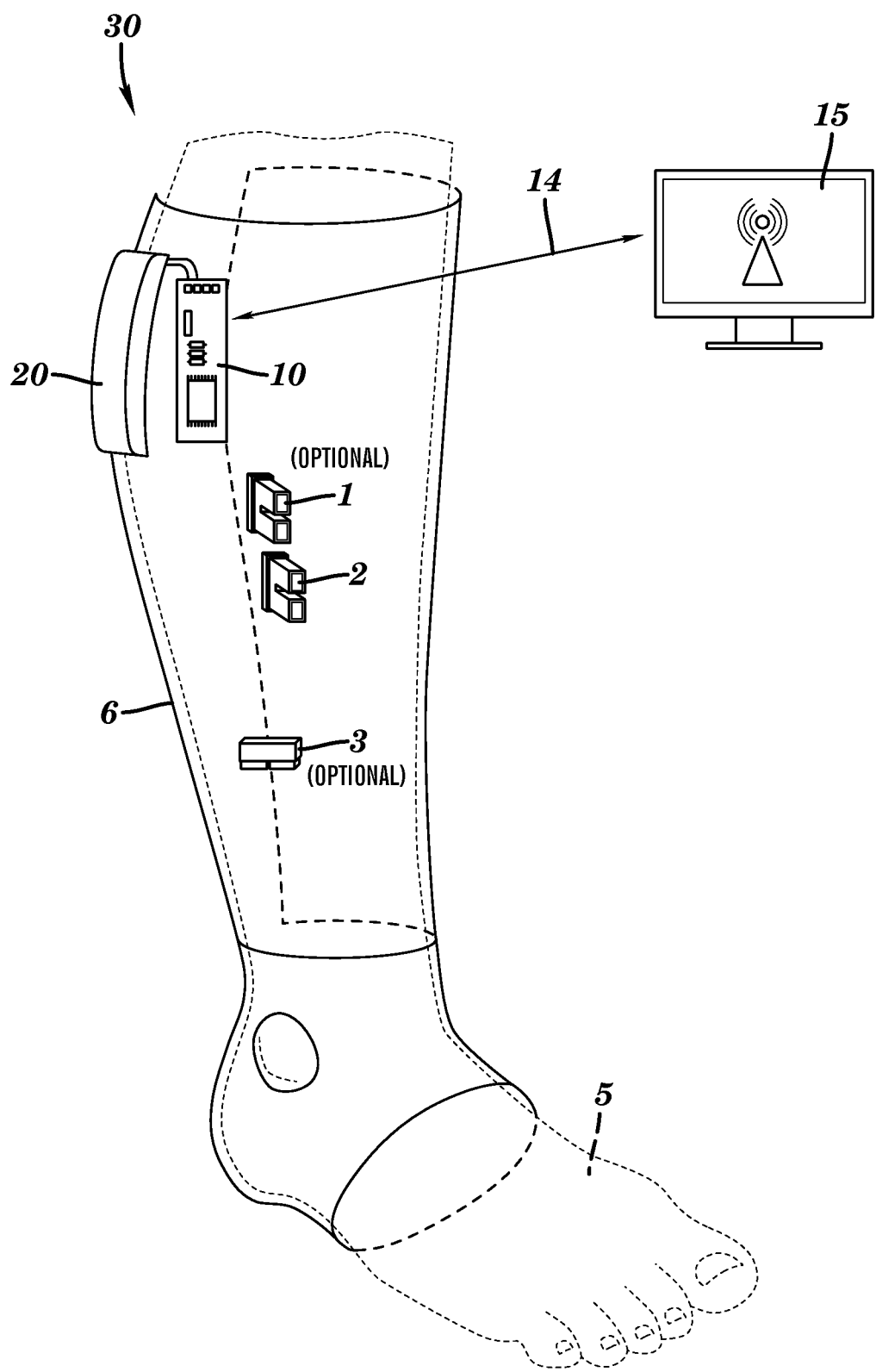
FIG. 1 is a partial perspective view of an exemplary portable system capable of terrain-and-gait monitoring while predicting upcoming terrain.

The system and method of the present invention utilizes one or more sensors to generate data attached to a user interfaced with a data monitoring computing device and a data management computing device. The system and method is capable of continuously and simultaneously monitoring the terrain the user is traversing and gait pattern with which the user is traversing the terrain, in addition to predicting the upcoming terrain the user is about to traverse. As used herein, "gait pattern" is a combination of the step frequency and the motion of the leg as the user steps. An exemplary wearable, portable system, which is capable of terrain-and-gait monitoring while predicting upcoming terrain is illustrated in FIG. 1. While FIG. 1 shows three sensors, this embodiment is for illustrative purposes only as the system may include one or more sensors in accordance with the invention as further detailed herein. Thus, for example, sensors 1 and 3 are labeled optional in FIG. 1. The system 30 includes one or more sensors, as illustrated by sensors 1-3, attached to one leg 5, as illustrated in FIG. 1, or both legs of a walking person, interfaced to a data monitoring computing device 10 and data management computing device 15 by a data transfer interface 14, and powered by a portable power source 20. The one or more sensors can be attached anywhere on the leg, preferably the lower leg below the knee. The system 30 can include other types and numbers of systems, devices, components or other elements in other configurations in the spirit of the present invention. This technology provides a number of advantages including providing a method and system for effectively monitoring terrain and gait simultaneously while predicting upcoming terrain. Preferably, components of the system are mounted on a substrate 6, which is attached to the user, although other techniques for attaching components of the system to the user can be used.

In one embodiment, the system 30 includes a single sensor to generate data, for example, sensor 2 only as shown in FIG. 1. When a single sensor is used, a suitable sensor for use in the present invention includes a proximity sensor capable of generating terrain data indicating the distance between the sensor and approaching terrain. Accordingly, the single sensor 2 is preferably positioned to generally face ahead of the individual, preferably from at least one step ahead to several steps ahead. Suitable proximity sensors include infrared sensors, ultrasonic sensors, and laser sensors, more preferably a GP2Y0A02YK infrared range finder.

Figure 2:
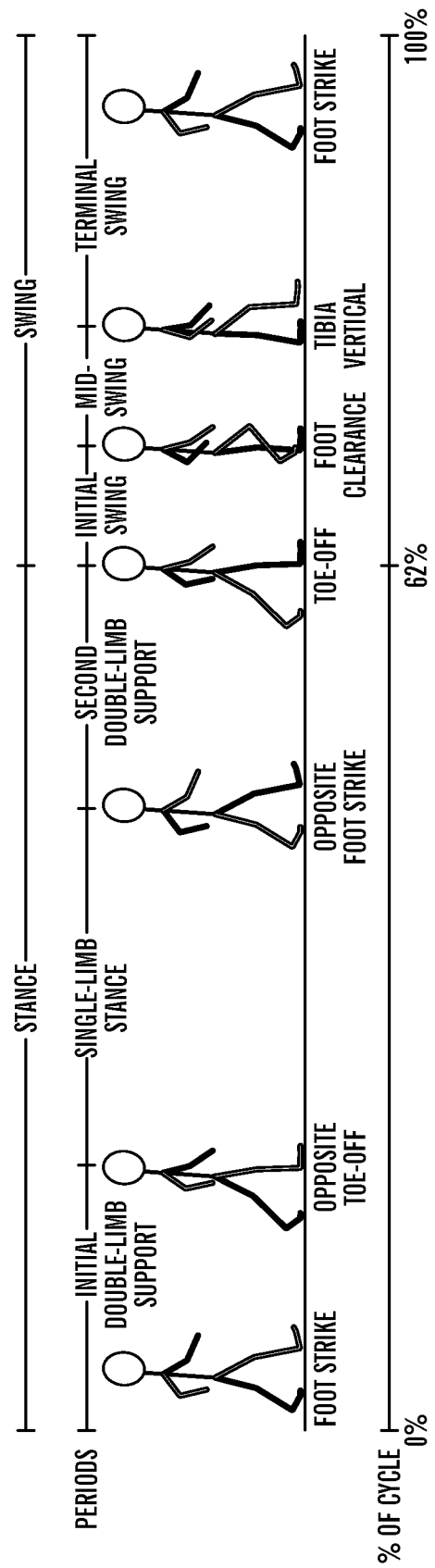
FIG. 2 is an illustration of a body shown walking through a complete gait cycle.

In this embodiment, the data from single sensor 2 contains a pattern that repeats whenever the instrumented leg is on the ground during the stance phase as shown in FIG. 2. For example, at the time of heel strike as shown in FIG. 2, the single sensor 2 will be at a point in the gait cycle closest to the ground, and will give a high reading. The same will be true every time the user's heel strikes the ground. The recurrence of this pattern can be used to establish periodicity of gait of the user while traversing the terrain. Thus, in this embodiment, a single sensor generates terrain data as well as gait speed data and is capable of monitoring the terrain and the gait of the user traversing the terrain.

In another embodiment, the system 30 includes more than one sensor, for example, two sensors 2 and 3 to generate terrain and gait speed data, as shown in FIG. 1. In this embodiment, the first sensor 3 is used to establish periodicity of gait. Suitable sensors include those capable of generating high/low data in the gait cycle to calculate the period of the gait, such as for example, a GP2D12 infrared sensor, although other types of sensors can be used. The first sensor 3 is preferably positioned below the knee on the lower leg of a human, oriented toward the ground; for example, so as to switch from low to high at the point in the gait cycle where the sensor on the user's lower leg is closest to the ground during the stance phase as shown in FIG. 2. This provides an indication of gait period, as the high point is only triggered once during the gait cycle when a threshold value is exceeded.

In this embodiment, the second sensor 2 is a proximity sensor used to detect the distance between the sensor and the approaching terrain. The second sensor 2 is, for example, a GP2Y0A02YK infrared range finder that measures the distance between itself and the terrain ahead of the walking person 5, although other types of sensors can be used. Accordingly, the second sensor 2 is positioned to generally face ahead of the individual, preferably from at least one step ahead to several steps ahead.

Optionally, the system 30 can contain for example a third sensor (1), preferably a proximity sensor, used to gather other environmental information, although the system can contain more than three sensors or other types and numbers of sensors to gather other types of data. For example, this third sensor could be placed on the lower leg positioned to generally face ahead of the individual, as shown in FIG. 1 or other lower limb segments (foot or thigh) to collect additional kinematic gait information; it could be used to improve the accuracy of terrain forecasting, by looking at a different point either ahead of or behind the person, and corroborating the second proximity sensor data; it could be used to monitor placement of a cane or walker, to help train people to use these aids properly.

Each of the exemplary sensors 1-3 are preferably powered by a portable power source 20, such as a rechargeable battery and are coupled to the data monitoring computing device 10 to transmit data relating to the gait cycle and the type of terrain the person 5 is traversing, although the sensors could be powered in other manners and coupled to other types and numbers of systems, device, components, or other elements.

The data monitoring computing device 10 includes a processor, memory storage device and an interface system which are coupled together by bus or other link, although other types and numbers of computing devices, such as an external computing device, for example, data management computing device 15 can be used in place of or in combination with the data monitoring device and one or both can be attached or not attached to the individual, by way of example. The processor in the data monitoring computing device 10 executes a program of stored instructions for one or more aspects of the present invention as described and illustrated herein, although the processor could execute other numbers and types of programmed instructions. The memory storage device in the data monitoring computing device 10 stores these programmed instructions for one or more aspects of the present invention as described and illustrated herein, although some or all of the programmed instructions could be stored and/or executed elsewhere. A variety of different types of memory storage devices, such as a random access memory (RAM) or a read only memory (ROM) in the system or a floppy disk, hard disk, CD ROM, or other computer readable medium which is read from and/or written to by a magnetic, optical, or other reading and/or writing system that is coupled to the processor in the gait and terrain monitoring system can be used for the memory storage device in the gait and terrain monitoring device.

The data interface system 14 in the data monitoring computing device 10 is used to operatively couple and communicate between the data monitoring computing device 10, the sensors 1-3 and the data management computing device 15, although other types and numbers of communication networks or systems with other types and numbers of connections and configurations to other types and numbers of systems, devices, and components can be used. By way of example only, the one or more communication networks can be one or more direct connections although other types and numbers of communication networks, such as a local area network, a wide area network, modems and phone lines, e-mail, and wireless communication technology, each having their own communications protocols, can be used.

The data management computing device 15 includes a processor, memory storage device and an interface system which are coupled together by bus or other link, although the computing device may comprise other types and numbers of elements in other configurations, such as a computing device attached to the individual, for example, data monitoring computing device 10 can be used in place of or in combination with the data management device and one or both can be attached or not attached to the individual, by way of example. The processor in the data management computing device 15 executes a program of stored instructions for one or more aspects of the present invention as described and illustrated herein, although the processor could execute other numbers and types of programmed instructions. The memory storage device in the data management computing device 15 stores these programmed instructions for one or more aspects of the present invention as described and illustrated herein, although some or all of the programmed instructions could be stored and/or executed elsewhere. A variety of different types of memory storage devices, such as a random access memory (RAM) or a read only memory (ROM) in the system or a floppy disk, hard disk, CD ROM, or other computer readable medium which is read from and/or written to by a magnetic, optical, or other reading and/or writing system that is coupled to the processor in the gait and terrain monitoring system can be used for the memory storage device in the gait and terrain monitoring device.

The interface system 14 in the data management computing device 15 is used to operatively couple and communicate between the data management computing device 15 and the data monitoring computing device 10, although other types and numbers of communication networks or systems with other types and numbers of connections and configurations to other types and numbers of systems, devices, and components can be used. By way of example only, the one or more communication networks can be one or more direct connections although other types and numbers of communication networks, such as a local area network, a wide area network, modems and phone lines, e-mail, and wireless communication technology, each having their own communications protocols, can be used.

Although the data monitoring computing device 10 and the data management computing device 15 are described and illustrated herein, other types and numbers of data monitoring and data management computing devices in other topologies can be used. It is to be understood that the systems of the examples described herein are for exemplary purposes, as many variations of the specific hardware and software used to implement the examples are possible, as will be appreciated by those skilled in the relevant art(s).

Furthermore, each of the systems of the examples may be conveniently implemented using one or more general purpose computer systems, microprocessors, digital signal processors, and micro-controllers, programmed according to the teachings of the examples, as described and illustrated herein, and as will be appreciated by those ordinary skill in the art.

In addition, two or more computing systems or devices can be substituted for any one of the systems in any example. Accordingly, principles and advantages of distributed processing, such as redundancy and replication also can be implemented, as desired, to increase the robustness and performance of the devices and systems of the examples.

The examples may also be implemented on computer system or systems that extend across any suitable network using any suitable interface mechanisms and communications technologies, including by way of example only telecommunications in any suitable form (e.g., voice and modem), wireless communications media, wireless communications networks, cellular communications networks, Public Switched Telephone Network (PSTNs), Packet Data Networks (PDNs), the Internet, intranets, and combinations thereof.

The examples may also be embodied as non-transitory computer readable medium having instructions stored thereon for one or more aspects of the technology as described and illustrated by way of the examples herein, which when executed by a processor (or configurable hardware), cause the processor to carry out the steps necessary to implement the methods of the examples, as described and illustrated herein.

An exemplary method for monitoring terrain and gait, preferably, simultaneously and continuously, will now be described. In this particular embodiment, the user is walking, although this technology can be used in a variety of different types of applications, such as with running, cycling, or cross-country skiing, by way of example only. This technology can be used in traversing a variety of different types of terrain: level ground; up and down stairs; and up and down a ramp, by way of example only. Additionally, in this embodiment one set of two sensors 2 and 3 is described, although other numbers of sets of sensors, such as one for each leg could be used and other numbers of sensors in each set could be used, such as one sensor or three sensors. In this illustrative embodiment, as the person walks, the first proximity sensor 3 provides a measure of gait speed, the second proximity sensor 2 provides a repeated pattern of measurements that is dependent on the terrain being traversed and the gait characteristics of the person. Optionally, a third sensor 1 can provide additional data, such as terrain information to improve prediction accuracy, gait information to gather information about the position of the foot or lower leg, or the location of an assistive device (such as a cane or walker) relative to the person.

Data from the sensors 2 and 3 is transmitted to the data monitoring computing device 10, where exemplary stored programmed instructions are used to process the data from the sensors to define the gait cycle and identify the type of terrain the person 5 is traversing. The data from the sensors also may be transferred via a data transfer interface 14 to a data management computing device 15 to display or further analyze the data, such as to define the gait cycle and identify the type of terrain the person 5 is traversing.

The data monitoring computing device 10 also may analyze the incoming data from the sensors 2 and 3 during each gait cycle and determine whether or not the characteristic gait patterns of the person on a particular terrain has changed over time. The data monitoring computing device 10 may also determine and record the person's average gait speed and the fraction of walking time spent on each different type of terrain. Further, the data monitoring computing device 10 may store the received data from the sensors 2 and 3 for later processing by the data monitoring computing device 10 or another computing device, such as data management computing device 15 which may perform identical operations to those being performed by the data monitoring computing device 10. This data from the sensors 2 and 3 can be transferred by USB connections or in other manners, such as wirelessly by way of example only. In another example, the data monitoring computing device 10 could be equipped with a wireless transmitter that would allow it to link to a mobile device that could provide clinicians with patient updates in between clinic visits, or allow patients to see a log of their progress over a daily, weekly, monthly, or other set time period, although the data could be transmitted in other manners, such as by hard wire connections, or by removable flash memory to other devices, in other time frames.

In another embodiment of this technology, a second set of one or more sensors which are the same in structure and operation as, for example, sensors 1-3 as illustrated and described herein are attached to the opposite leg of the person. This enables the data monitoring computing device 10 to obtain the data from both sets of sensors, compare the motion of the two legs which are both covering the same terrain and then use both to determine gait cycle and to identify the type of terrain. By way of example, when this technology is implemented on both legs of a person, it could be used to monitor symmetry (or asymmetry) in gait patterns of the person by the data monitoring computing device 10 comparing the data from the two sets of sensors. The optional second set of sensors would also enable, for example: monitoring whether a person is preferentially using one leg over another for tasks such as leading up or down stairs or ramps, stepping over obstacles; measure changes in steppage gait, which is a specific example of a type of asymmetry.

In another embodiment of this technology, this embodiment would be the same as the first embodiment illustrated and described above, except two GP2Y0A02YK infrared range finders, by way of example, would be used as sensors on the same leg. One or both of the sensors used to collect terrain data could be used to identify periodicity as well, and terrain prediction could be based on data from the two sensors being in agreement. This would improve reliability of the prediction algorithm used to predict upcoming terrain.

By way of example only, this technology can be used in a number of ways, such as a rehabilitation monitor. This technology used as a rehabilitation monitor can be made inexpensively enough that it can be sent home with patients to monitor their assigned exercises in between clinic visits. The device, as described in the examples herein, can monitor average gait speed, changes in gait speed, deviations from a person's typical gait pattern, total time spent walking, total time spent in higher intensity exercise (steps, ramps, other non-level terrain), and fraction of exercise time spent in higher intensity activity.

In another example of this technology, it could be attached to an active ankle-foot or knee-ankle-foot orthotic that provides signals based on data from the sensor to adapt the wearer's foot position to the approaching terrain. This can help to create a more natural gait pattern. Similarly, this technology could be used with a prosthetic lower limb to provide signals to adapt the limb to the determined gait speed and identified upcoming terrain. This can help to create a more natural gait pattern.

In another example of this technology, it could be attached to a cyclist's foot or lower leg to monitor a combination of cadence and body position during cycling over different types of terrain. This could help cyclists optimize their performance by improving form. Similarly, this technology could be used to optimize performance for any athlete who needs to adjust a repetitive motion in order to adapt to changing terrain, for example: cross-country running, hurdling, or cross-country skiing.

As discussed earlier, the data monitoring computing device 10 is able to identify the type of upcoming terrain based on data from one or more of the sensors 1-3. An embodiment of this identification is discussed below. First, sensor data is collected from an individual walking over each of the different terrain types. The sensor data includes information about the gait speed, or the frequency with which steps are being taken, which can be determined based on the time between consecutive switches from "low" to "high" of, for example, sensor 3 in FIG. 1. The sensor data also includes proximity sensor measurements throughout the gait cycle from, for example, sensor 2 in FIG. 1. These data are used to calibrate the system to the individual. Models for the ground conditions can be established by the data monitoring computing device 10 representing each type of traversed ground condition with a Fourier series created using, for example, a RANdom SAmple Consensus (RANSAC) technique. In this embodiment, a fourth order Fourier series, shown in Equation (1), is used to fit the gait speed data. The Fourier series is a periodic function, with a base frequency equal to the gait speed, $\omega$. The equation is constructed of the sum of sinusoidal functions that each contribute value at a different frequency, $n\omega$. A fourth order Fourier series contains frequency content at the base frequency, as well as multiples of the base frequency up to $4\omega$. The relative contribution of signal at a given frequency is determined by the value of the coefficients, $a_n$ and $b_n$. Fourier series are ideal to model gait because they are periodic in nature, just as a person's gait pattern is periodic, and they can be scaled in time, just as a person's gait patterns are similar whether they are walking slightly faster or slightly slower. As noted above, gait speed can be measured using another sensor, such as sensor 1 shown in FIG. 1, to determine when the foot is in contact with the ground. Once this initial calibration is completed for the individual, different terrain models are established for a variety of terrain types and the monitoring computing device 10 can take in data live and give an assertion as to which type of terrain the person is walking over, using pattern recognition techniques and comparing incoming data to the calibration data of the terrain models.

$$G(t) = a_0 + \sum_{n=1}^{4} a_n \cos(n\omega t) + b_n \sin(n\omega t) \quad (1)$$

Additionally, this technology may also predict an upcoming change in the type of terrain from, for example level walking to walking down a ramp based on stored correlation tables. With this prediction, an orthotic or prosthetic device could then be made to adjust itself based on the predictive information provided by the data monitoring computing device 10 giving the user a more natural gait, even when encountering adverse conditions. A by-product of constantly using a person's own gait to measure ground type is the ability to track a person's changing gait pattern over time. This can be done by analyzing the difference between the coefficients in the original calibration data and coefficients from future data taken over a known terrain such as level ground. The ability to track gait pattern changes in real time gives therapists a valuable new tool for tracking patient progress by producing more quantitative data sets.

Referring to FIG. 2, the figure shown is illustrated as a walking body. A complete gait cycle is shown as % of cycle. This figure provides perspective to the time frame within which this system operates. A full prediction of upcoming terrain can be produced at approximately 60% of the gait cycle or before toe-off.

EXAMPLE

This example used a prototype corresponding in structure and operation to the terrain-and-gait monitoring system as shown in FIG. 1, except only sensors 2 and 3 were used. Sensor data was collected for a male subject with normal gait for the following walking scenarios: (1) Level Walking: Record for approximately 20 seconds—avoid walking right next to walls or chair legs, as these objects may cause sensor artifacts; (2) Up and Down Stairs: Record a flight of stairs, making sure to lead with whatever leg is not wearing the device as this will likely be the case for someone with impaired gait; and (3) Up and Down Ramps: Record for approximately 20 seconds up or down a ramp. For each scenario, many individual steps were taken. These steps were each scaled in time to a common gait speed by adjusting the $\omega$ value. Using the RANSAC curve fitting technique, the time-shifted steps were fit to fourth order Fourier series. This resulted in a set of Fourier coefficients $a_0$-$b_4$ for each step over each terrain type. The set of each coefficient's mean values for a given terrain type represent a calibration curve for an individual's typical gait pattern over that given terrain type. Exemplary results from testing with this prototype are set forth below:

Results: Characterization of Gait/Terrain Curves

Figure 3:
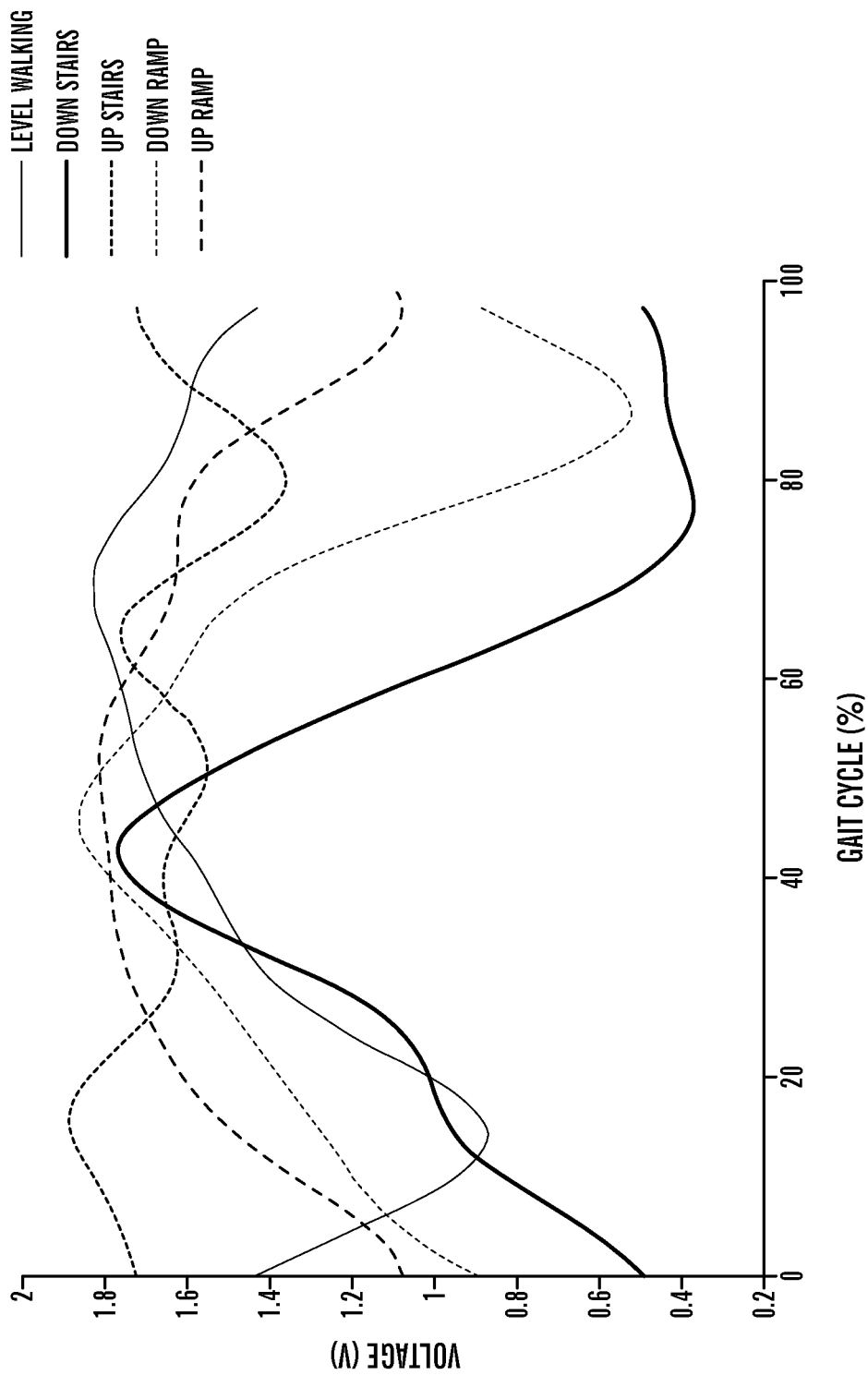
FIG. 3 is a graph showing gait curve calibration models of the system through various terrain types.

Referring to FIG. 3, a graph of the distinct signals that were measured for a single person traversing five different types of terrain: level ground; up and down stairs; and up and down a ramp. Each curve is an average of the curves generated from the raw data for each terrain type and represents the calibration of the system to the individual. The data was fit to fourth order Fourier series, which allowed a periodic function fit and scale of the data by frequency, i.e., gait speed.

Figure 4:
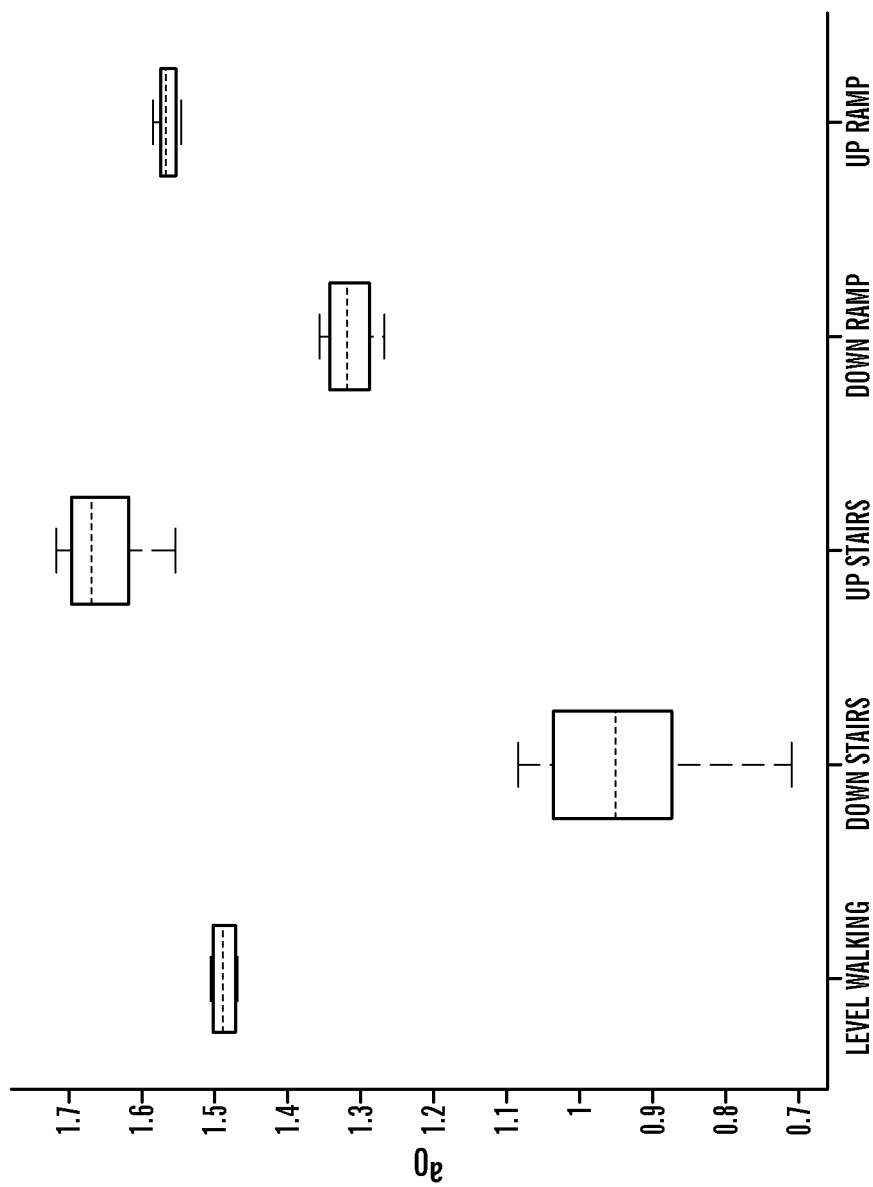
FIG. 4 is a box plot showing the differences in the first Fourier coefficients ($a_0$) used to characterize walking over each different type of terrain.
Figure 5:
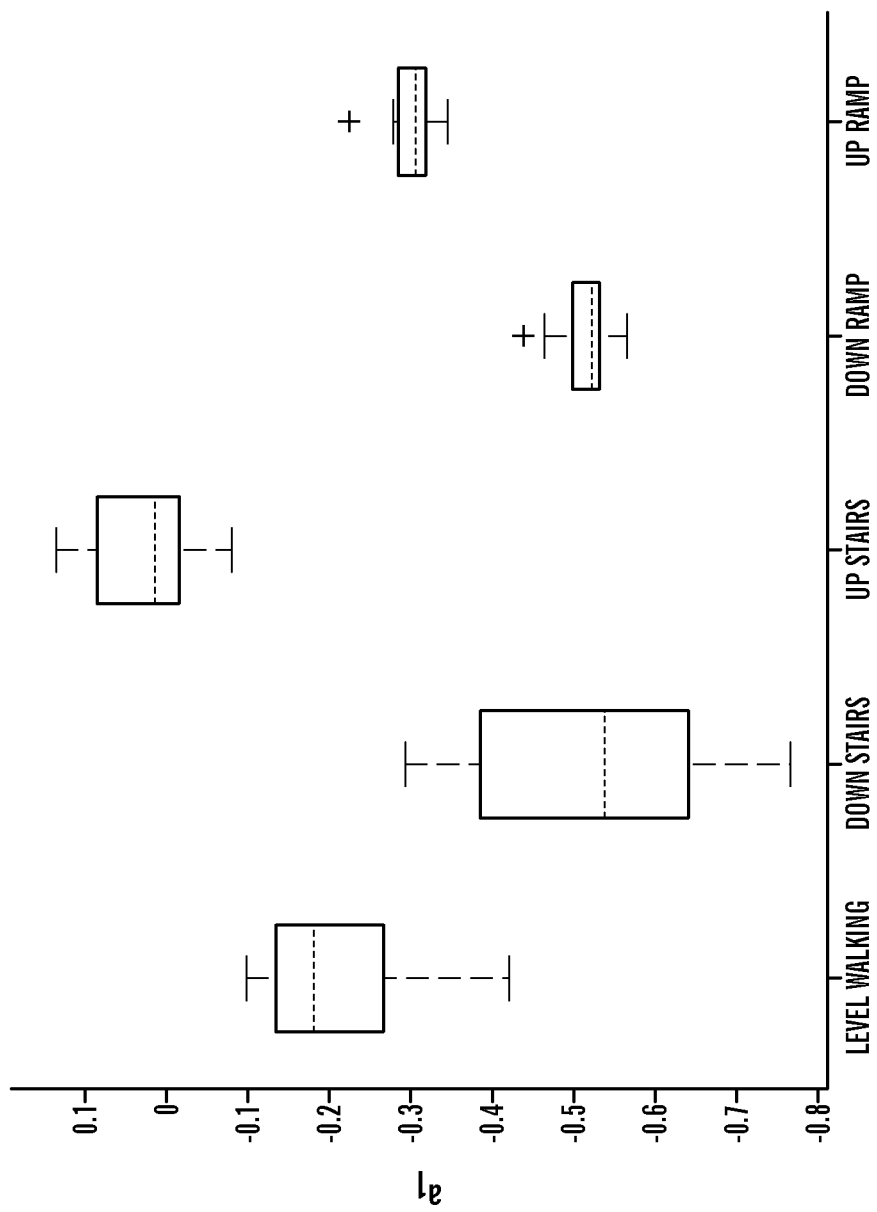
FIG. 5 is a box plot showing the differences in the second Fourier coefficient ($a_1$) used to characterize walking over each different type of terrain.
Figure 6:
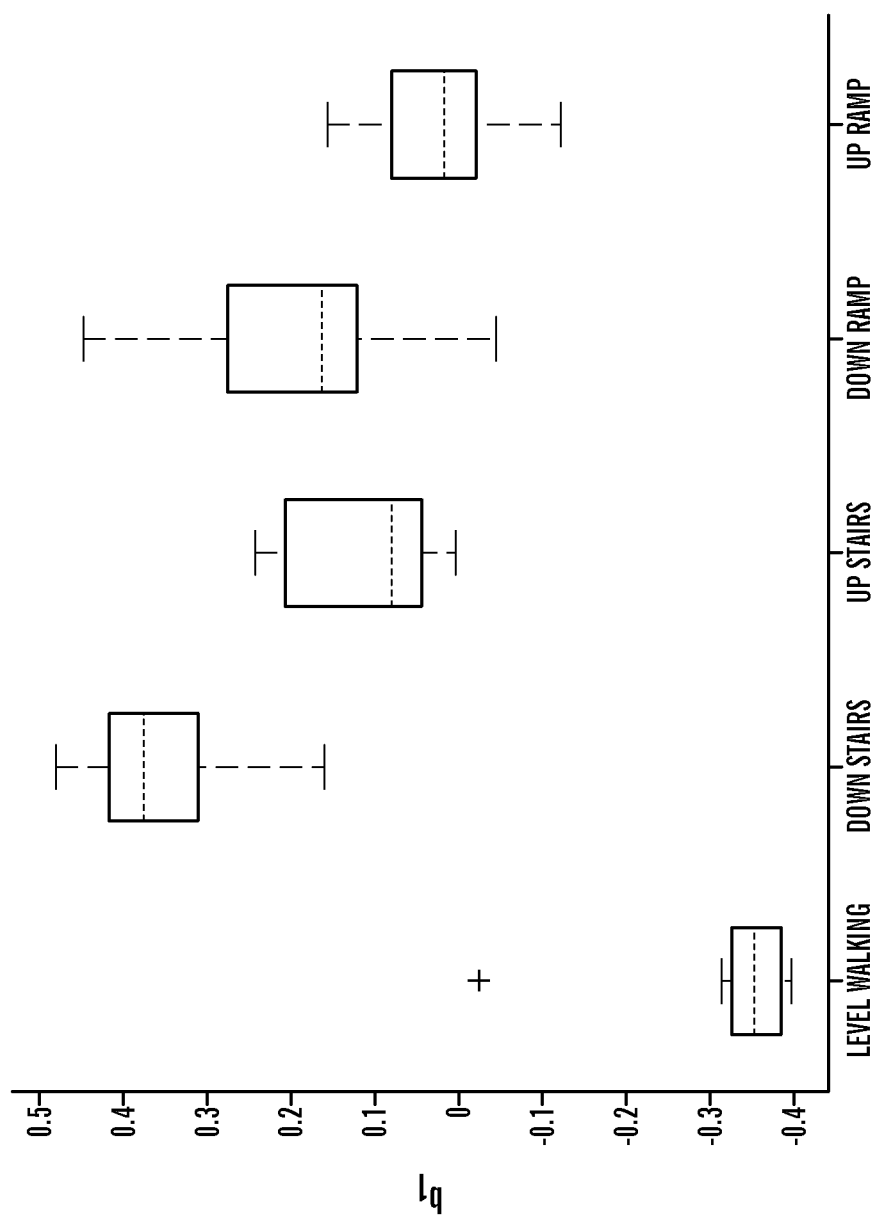
FIG. 6 is a box plot showing the differences in the third Fourier coefficients ($b_1$) used to characterize walking over each different type of terrain.
Figure 7:
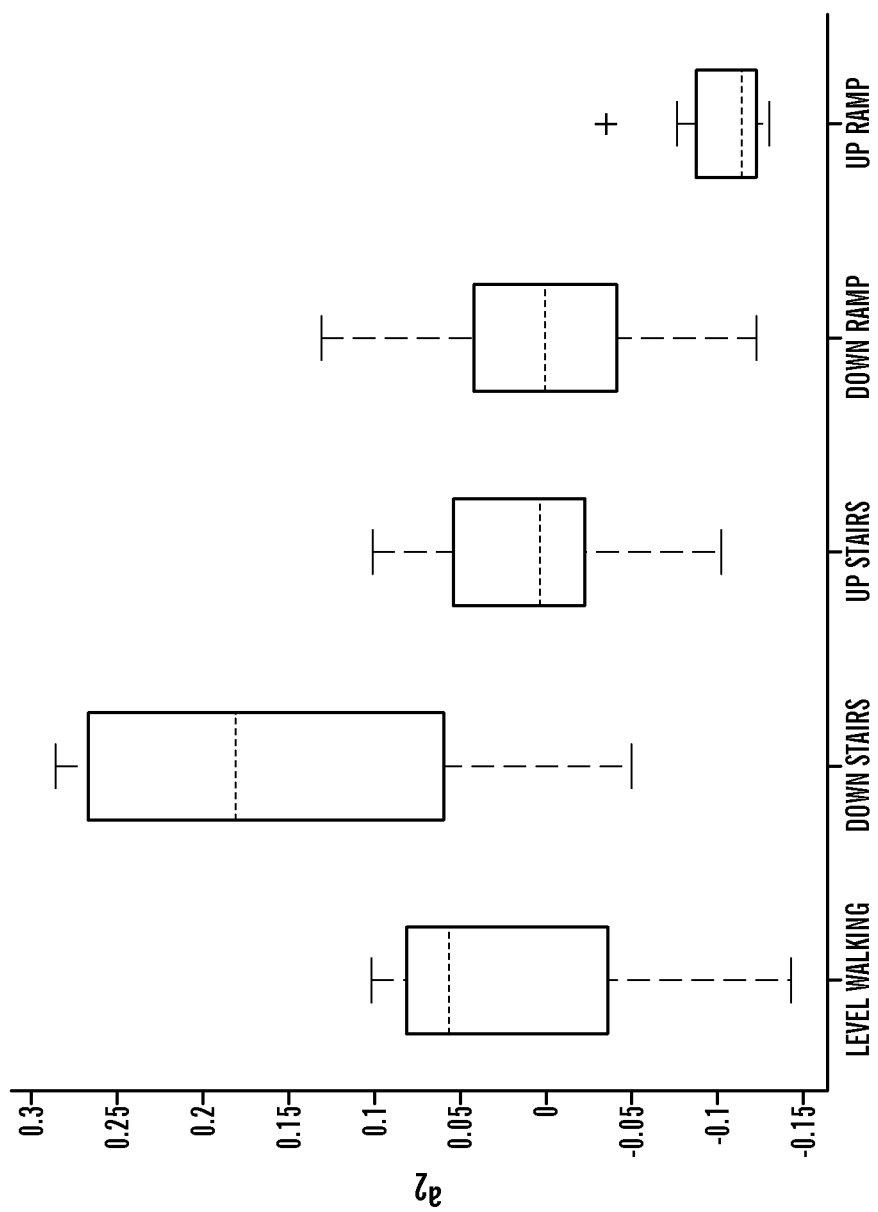
FIG. 7 is a box plot showing the differences in the fourth Fourier coefficients ($a_2$) used to characterize walking over each different type of terrain.
Figure 8:
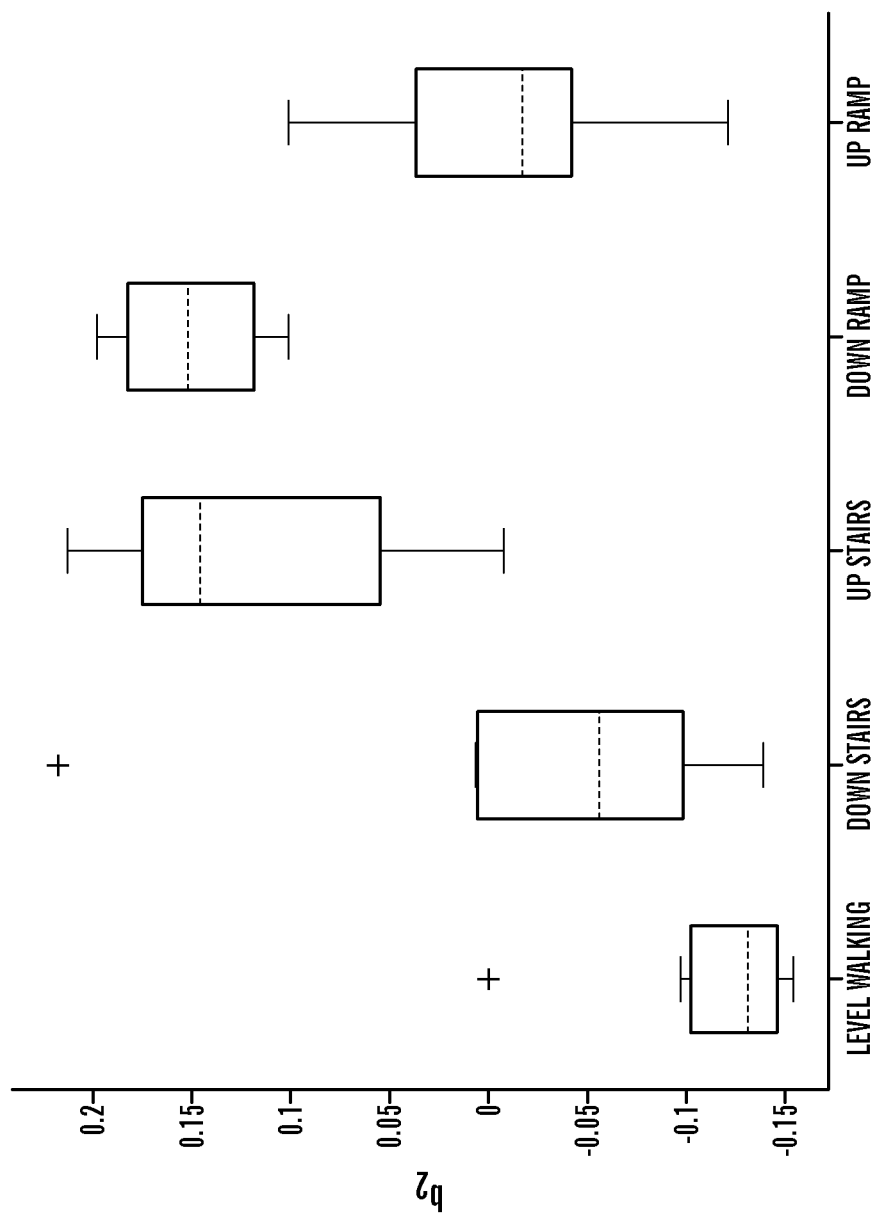
FIG. 8 is a box plot showing the differences in the fifth Fourier coefficients ($b_2$) used to characterize walking over each different type of terrain.
Figure 9:
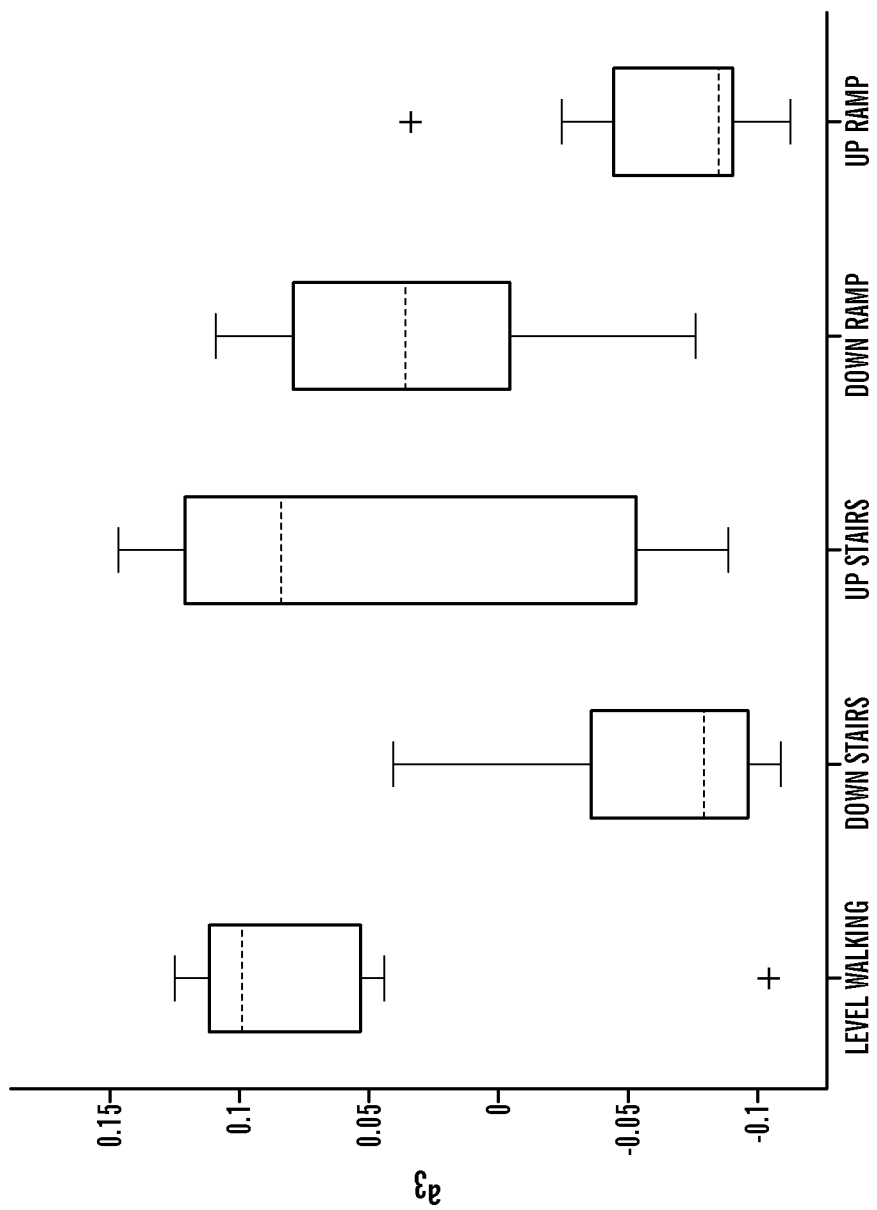
FIG. 9 is a box plot showing the differences in the sixth Fourier coefficients ($a_3$) used to characterize walking over each different type of terrain.
Figure 10:
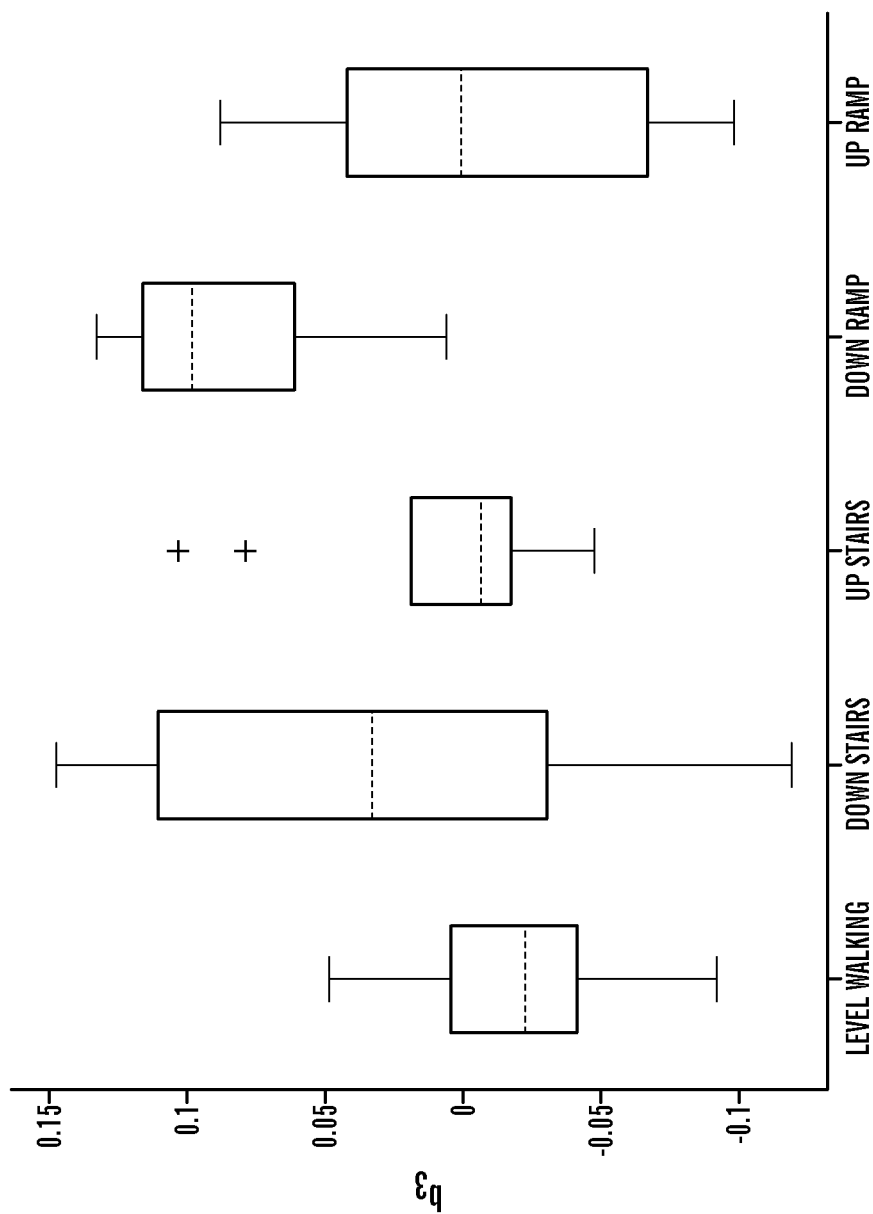
FIG. 10 is a box plot showing the differences in the seventh Fourier coefficients ($b_3$) used to characterize walking over each different type of terrain.
Figure 11:
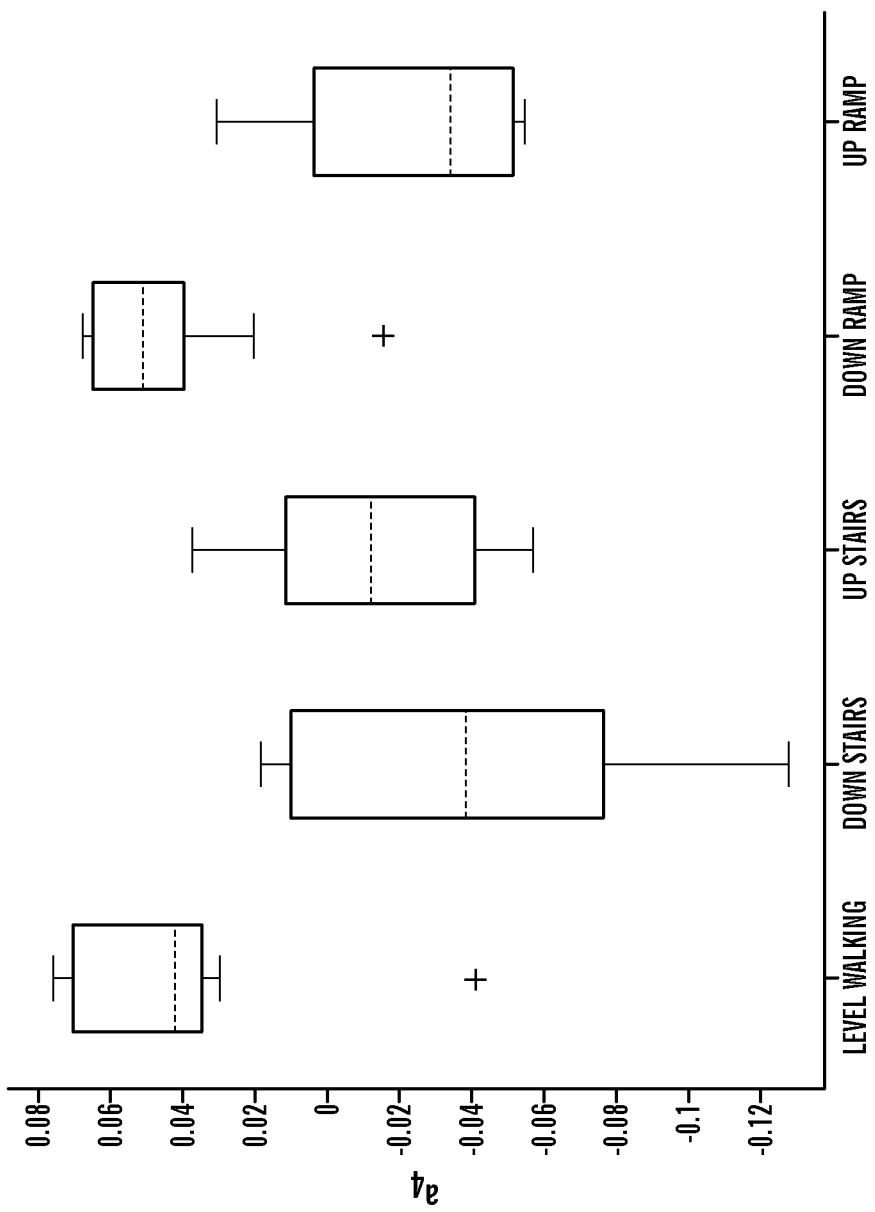
FIG. 11 is a box plot showing the differences in the eighth Fourier coefficients ($a_4$) used to characterize walking over each different type of terrain.
Figure 12:
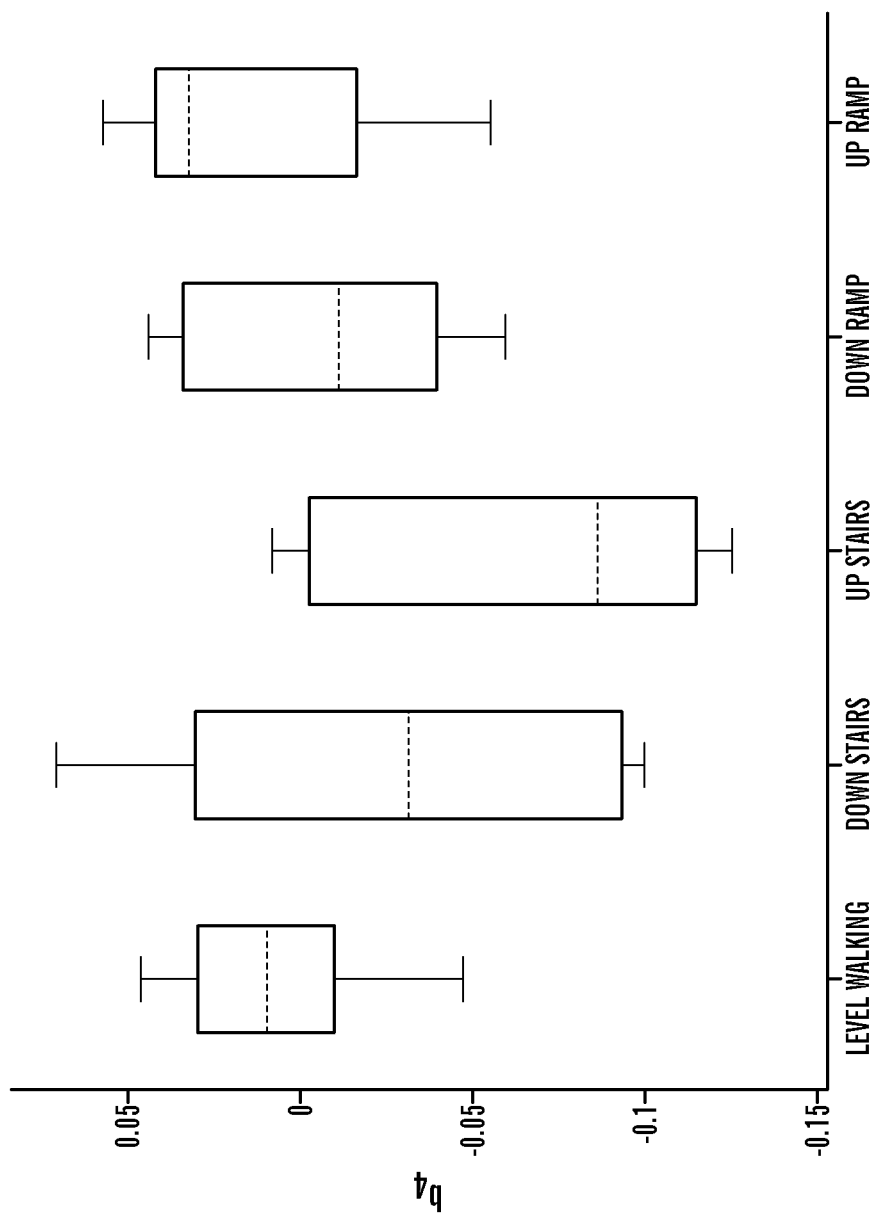
FIG. 12 is a box plot showing the differences in the ninth Fourier coefficients ($b_4$) used to characterize walking over each different type of terrain.

The nine Fourier coefficients $a_0$-$b_4$ as shown in the box plots in FIGS. 4-12 were used to plot the curves for each type of terrain shown in FIG. 3 for a specific individual. The box plots in FIGS. 4-12 show a summary of curve fitting results from many steps taken over known terrain; that is, the calibration results. For example, FIG. 4 shows, for each terrain type, a compilation of the various values of $a_0$ found from curve fits to each of the user's steps. The box in the box plot represents the middle 50% of the values of $a_0$ found by fitting step data (i.e., the $2^{nd}$ and $3^{rd}$ quartiles of the data), and the line in the center of the box represents the median value. The "whiskers" represent the extent of all fitted values of the coefficient falling within 150% of the interquartile range above and below the box, and +'s represent outliers that lie beyond the whiskers.

The box plots in FIGS. 4-8 show a clear difference between the lower order Fourier coefficients ($a_0$-$a_2$, $b_1$-$b_2$) obtained for each terrain type. It is the differences in these coefficients that result in the clearly visible differences between the curves shown in FIG. 3. FIGS. 9-12 also show that the higher order Fourier coefficients ($a_3$-$a_4$, $b_3$-$b_4$) do not vary much between the different terrain types. This means the system generates suitable results using lower order Fourier series to model the data, and does not require a fourth order Fourier series. A reduction in the order of the Fourier series would reduce the time required to perform any analysis on the gait and terrain data.

Terrain Prediction Capability:

The example uses pattern recognition to compare voltage signals from the infrared range finders with the set of calibration models generated, as set forth in FIG. 3, from the raw calibration results, as set forth in FIGS. 4-12. First, the gait speed $\omega$ in terms of steps per second is estimated for a moving individual by the method described previously. Using the Fourier series model and calibration coefficients for each terrain type, and estimated value of ω, a model for the user's traversing over each of the five terrain types can be created. The system is used to monitor gait and terrain by collecting newly generated sensor data being read from the user traversing terrain and the data is compared to each of the five calibration models using, for example, a least minimum squares approach, as outlined in Equation 2. The calibration model that shows the smallest difference from the incoming data is identified as the terrain type being traversed. Thus, by comparing the sensor data generated with the calibration models, the system can identify the type of terrain being traversed.

Not only does this system monitor terrain and gait with the capability to analyze collected data and determine the type of terrain being traversed, but it also has the capacity to predict upcoming terrain once gait speed is determined from, for example, the first proximity sensor described earlier. Once gait speed is determined, the first approximately 60% of any future gait cycle is analyzed to identify upcoming terrain type. This 60% corresponds approximately to the duration of the stance phase, i.e., the time between heel strike and toe-off for the instrumented foot. The results shown in FIGS. 13-17 illustrate examples of successful predictions from Table 1 completed using approximately 60% of the gait cycle, i.e., data collected between heel strike and toe-off. Therefore, the terrain-and-gait monitoring system can predict terrain type before the foot enters swing phase, which is when an active orthotic or prosthesis would need to be actuated, or when a user would need to adapt their own leg position to accommodate an upcoming obstacle or terrain change.

A least minimum squares analysis is used to compute the error between the incoming data and the various terrain models. The model that gives the lowest error is identified as the upcoming terrain. The least squares model is shown in Equation (2), where t represents relative time; w represents the assumed frequency, at which the person is stepping, x(t) represents the local data, and $f_i(t,1/\omega)$ represents each of the different models. The 0.6 in the summation represents the fact that the error equation is looking at what it assumes is the first 60% of the gait cycle.

$$error_i = \sum_{t=0}^{t+.6w1/\omega} (x(t) - f_i(t, 1/\omega))^2 \quad (2)$$

By computing this error for each model, within a single step, the program is able to make a prediction of what kind of ground the person is about to traverse.

Ground Type Prediction:

Table 1 represents the percentage of correctly predicted ground types from the training data. A representative example of one of the correct steps for the # of steps evaluated in Table 1 is shown in FIGS. 13-17 for each of the different terrain types investigated.

TABLE 1

Terrain Prediction Summary

|  | Level Walking | Down Stairs | Up Stairs | Down Ramp | Up Ramp |
|---|---|---|---|---|---|
| Correct (%) | 94.9 | 90.0 | 80.0 | 97.5 | 82.8 |
| # of Steps evaluated | 98 | 50 | 50 | 80 | 70 |

Level Walking Predictions:

With this exemplary terrain-and-gait monitoring system, 98 steps were evaluated, 94.9% were correctly identified (i.e., the exemplary terrain-and-gait monitoring system was given data known to be from a level walking step and 94.9% of the time predicted that.)

Figure 13:
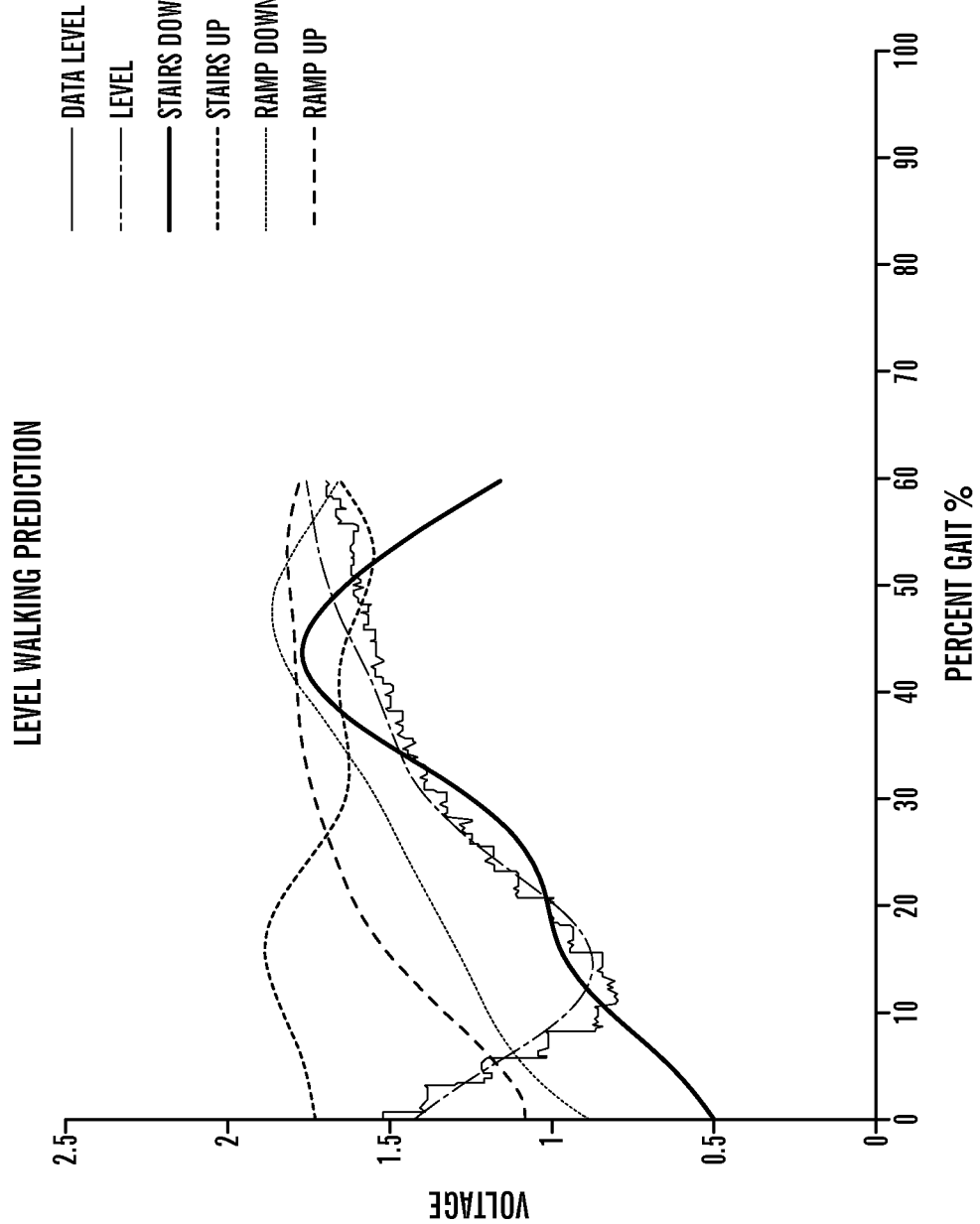
FIG. 13 shows a graph of an example of level walking prediction by an exemplary terrain-and-gait monitoring system.

An example of level walking prediction is shown in FIG. 13.

Figure 14:
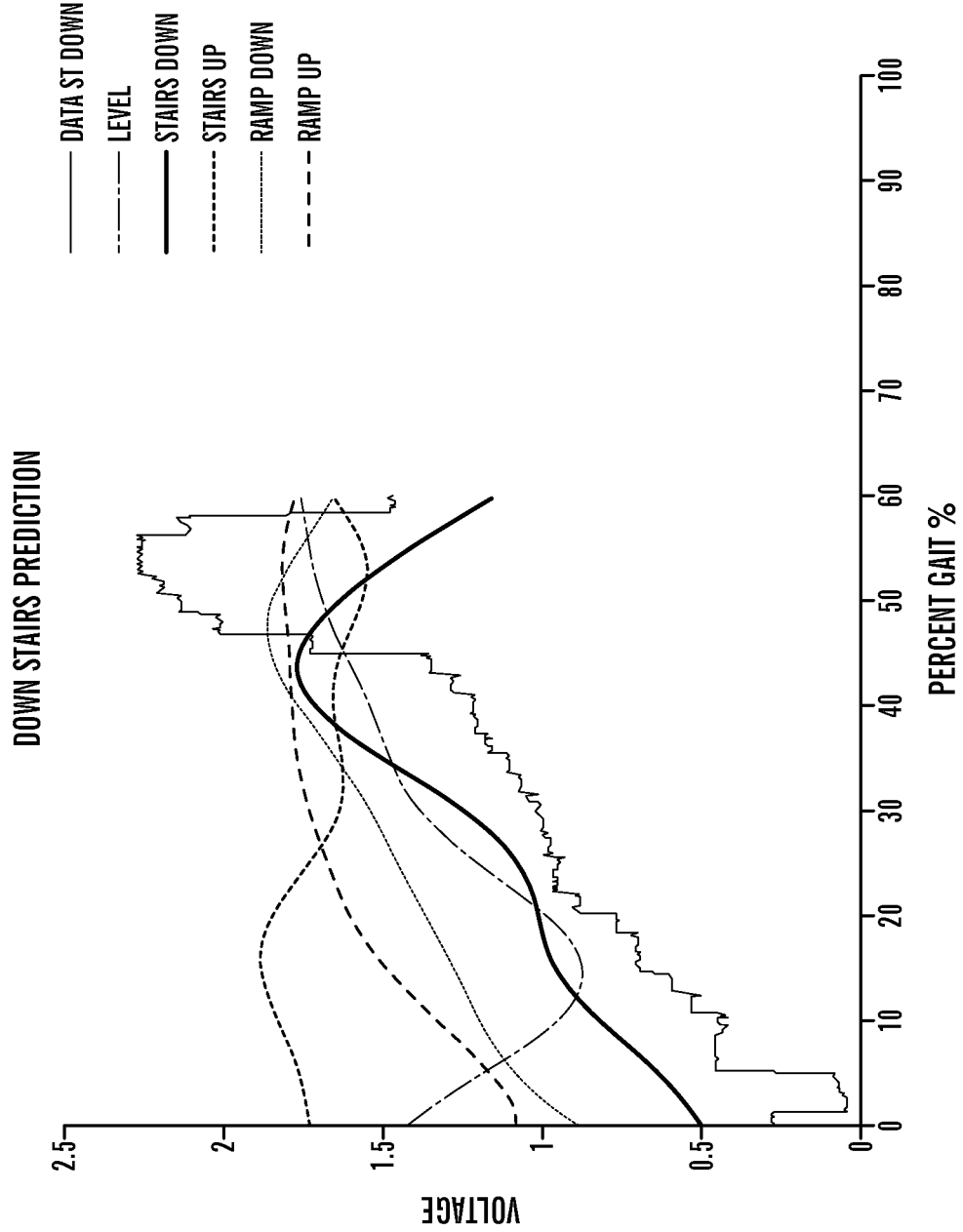
FIG. 14 shows a graph of an example of down stairs prediction by an exemplary terrain-and-gait monitoring system.

Down Stairs Predictions:

With this exemplary terrain-and-gait monitoring system, 50 steps were evaluated, 90% were correctly identified. An example of down stairs prediction is shown in FIG. 14.

Figure 15:
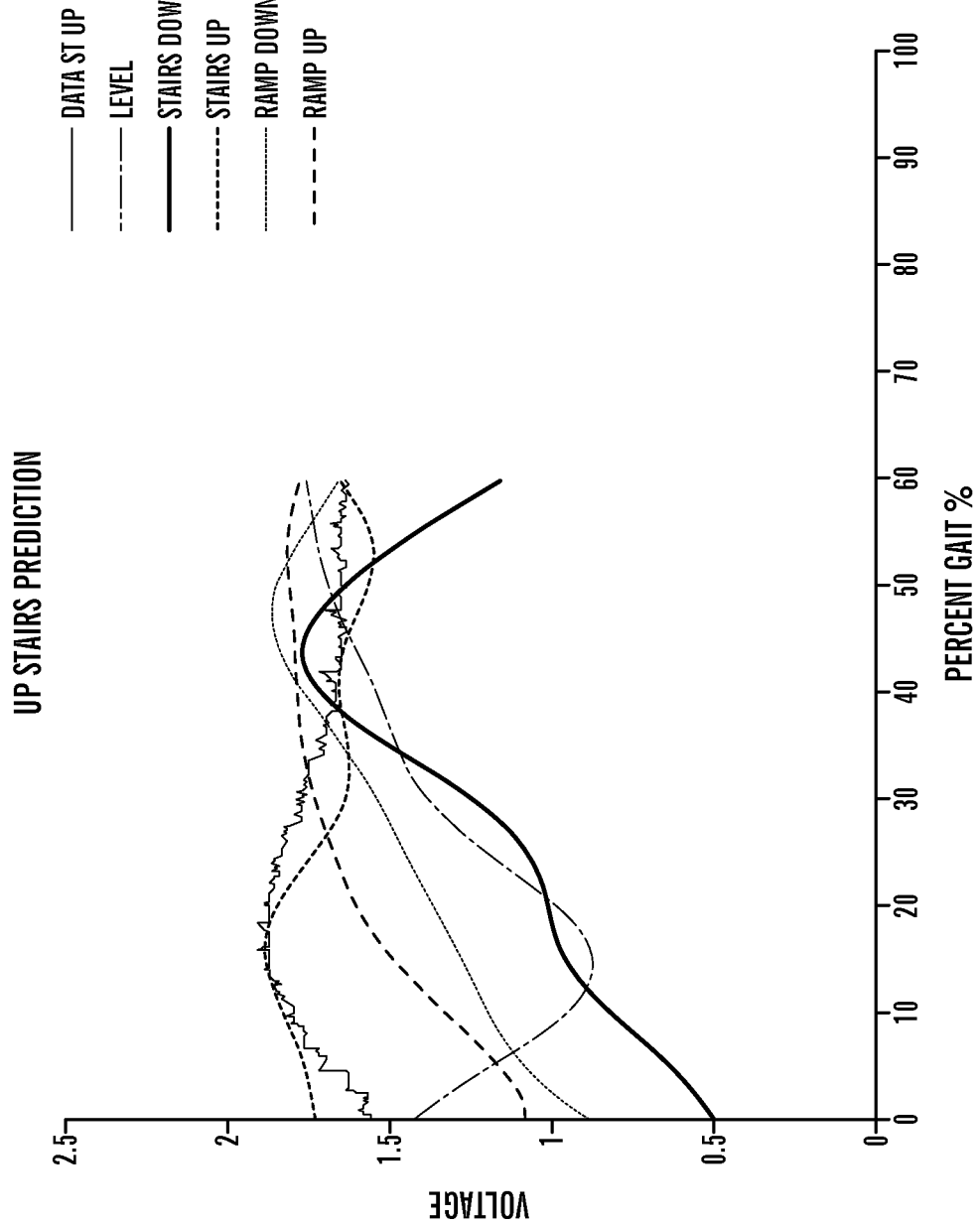
FIG. 15 shows a graph of an example of upstairs prediction by an exemplary terrain-and-gait monitoring system.

Up Stairs Predictions:

With this exemplary terrain-and-gait monitoring system, 50 steps were evaluated, 80% were correctly identified. An example of upstairs prediction is shown in FIG. 15.

Figure 16:
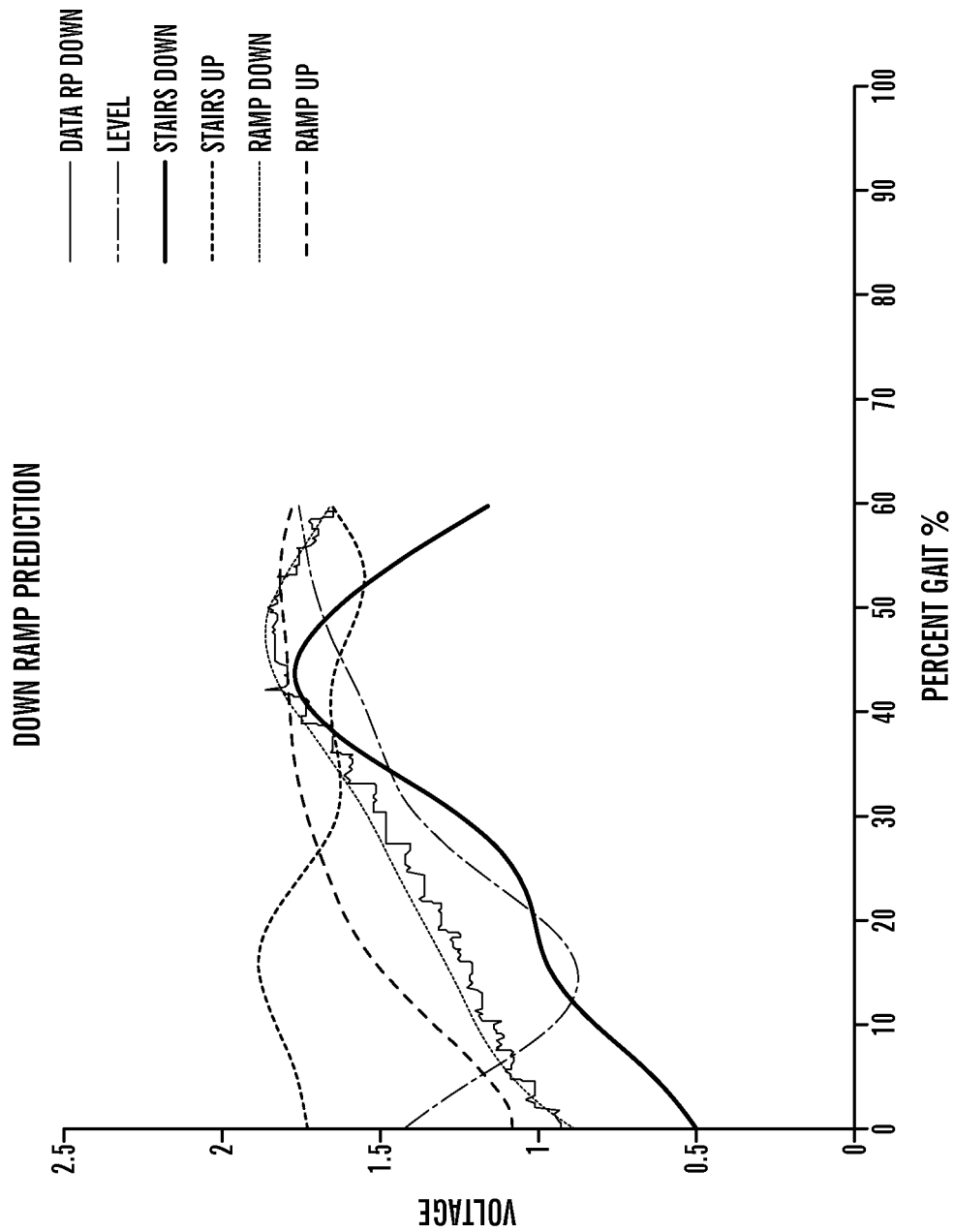
FIG. 16 shows a graph of an example of ramp down prediction by an exemplary terrain-and-gait monitoring system.

Down Ramp Predictions:

With this exemplary terrain-and-gait monitoring system, 80 steps were evaluated, 97.5% were correctly identified. An example of Down Ramp prediction is shown in FIG. 16.

Figure 17:
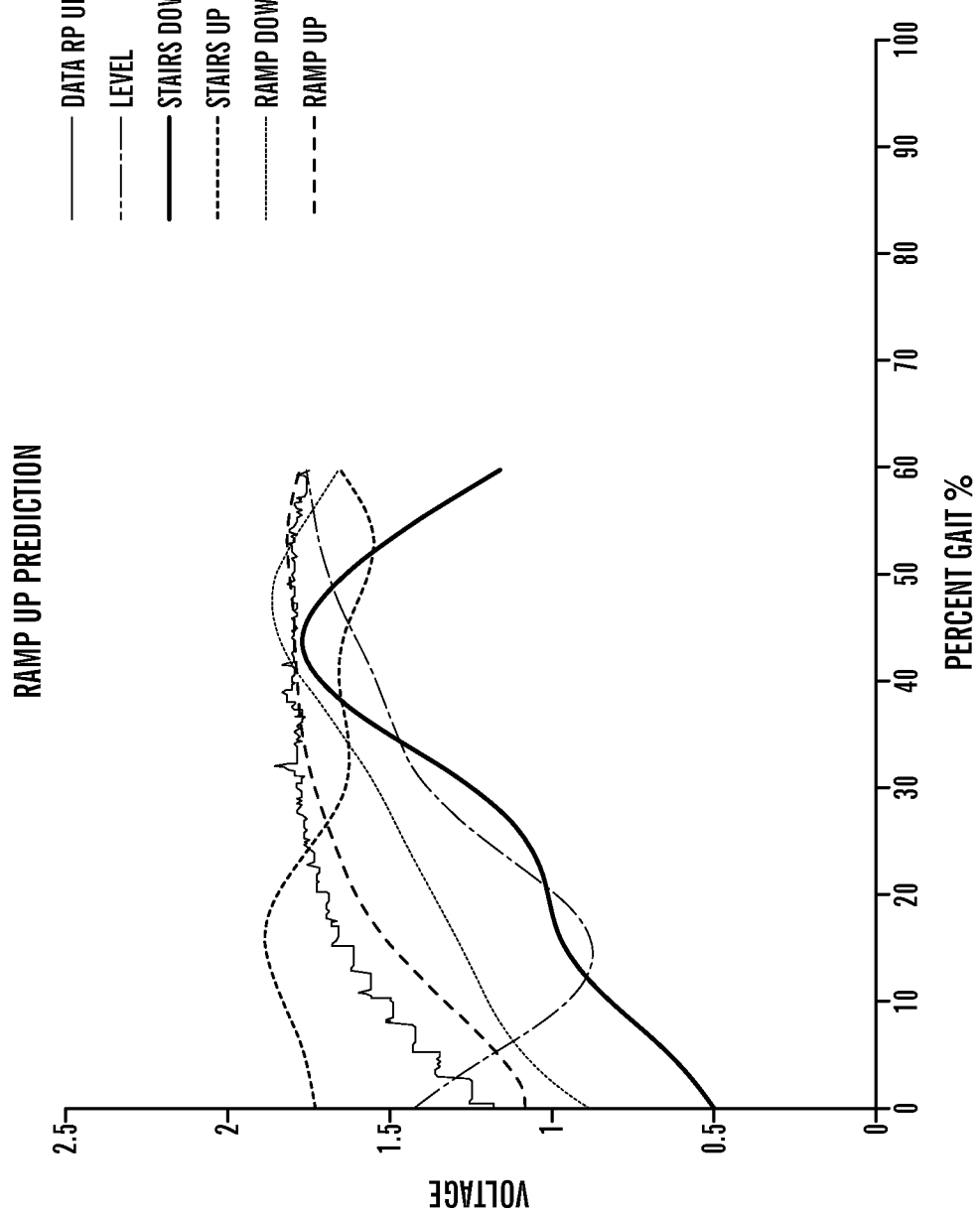
FIG. 17 shows a graph of an example of ramp up prediction by an exemplary terrain-and-gait monitoring system.

Up Ramp Predictions:

With this exemplary terrain-and-gait monitoring system, 70 steps were evaluated, 82.8% were correctly identified. An example of Up Ramp prediction is shown in FIG. 17.

Other examples of this technology may include improving the pattern recognition capability of this system, which would improve the accuracy of this system. Additionally, this technology could incorporate probability weighting. For example, the majority of your day is spent walking on level ground, therefore the error function could have a likelihood factor, making it much harder for level ground to be detected as anything, but level ground. This technology also could use time shift models for best fit. For example, instead of shifting all the models to get a minimum error for each an initial probability check can be done to eliminate false models. Following this by a time shift to reduce the remaining models errors to a local minimum could vastly improve predictions (there might not be enough time to complete this calculation within a single step). Further, this technology also could be implemented by attaching sensors to both legs. For example, given information about the position of both legs as described earlier, in scenarios where data from a single leg do not conclusively identify a single terrain type, data from the second leg can be used to help verify the terrain type.

This technology provides a number of advantages including providing a method and system for effectively continuously monitoring terrain and gait simultaneously. This technology utilizes one or more sensors and a management computing device. Suitable sensors for use in this technology are small and light and insensitive to interference from magnetic fields. The management computing device is able to analyze the data from the one or more sensors to define the gait cycle and in addition to identifying the type of terrain a person is traversing, to predict the terrain that the person is about to traverse during the next step.

The ability of this technology to capture interactions with the terrain makes this technology attractive for many applications, such as gait training, guidance for a blind person, and workout logging by way of example. Additionally, this technology can be utilized for gait and activity monitoring for home-based rehabilitation. Further, because this technology works based on one or more sensors directly measuring position of the leg as opposed to an accelerometer, for which voltage data would need to be integrated to get the required data, the computational power of this technology can be much lower than prior devices. This makes this technology more viable for portable applications than such prior devices.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A method for monitoring terrain and gait of a subject traversing terrain, the method comprising:
    characterizing a gait pattern of the subject traversing a plurality of terrain types for each of the plurality of terrain types traversed by:
    receiving by a management computing device a first terrain data from a first proximity sensor on a first appendage of the subject, comprising determining a distance between the first proximity sensor and a surface of an approaching terrain throughout a gait cycle of the subject while traversing each of the plurality of terrain types and receiving by the management computing device a first gait speed data relating to the gait of the subject from a first gait sensor on a second appendage of the subject throughout the gait cycle of the subject while traversing each of the plurality of terrain types to establish a periodic terrain model normalized by gait period by applying a periodic function to the first terrain data establishing gait speed as an independent variable to the periodic terrain model specific to the subject for each of the plurality of terrain types traversed, wherein the first and second appendages can be the same or different appendages;
    monitoring the gait pattern of the subject traversing a second terrain by receiving by the management computing device a second terrain data from the first proximity sensor and a second gait speed data from a second gait sensor to scale in time the periodic terrain model normalized by gait period to the incoming second gait speed data to identify the second terrain being traversed from established periodic terrain models;
    predicting an upcoming terrain by the management computing device from the received second gait speed data and the second terrain data for the subject; and
    providing a signal to the subject or a device worn by the subject based on the predicted upcoming terrain.

2. The method as set forth in claim 1 wherein the first proximity sensor and the first gait sensor are the same sensor.

3. The method as set forth in claim 1 wherein the first proximity sensor and the first gait sensor comprise at least two separate sensors.

4. The method as set forth in claim 1 further comprising defining a second gait cycle for the subject by the management computing device based on the second gait speed data and the predicting further comprises providing by the management computing device the second gait cycle.

5. The method as set forth in claim 4 further comprising identifying a type of terrain by the management computing device based on comparing the received second terrain data and the second gait cycle with calibrated terrain curves and the predicting further comprises providing by the management computing device the identified type of terrain traversed.

6. The method as set forth in claim 5 further comprising predicting a type of upcoming terrain by the management computing device based on comparing the received second terrain data and the second gait cycle over a portion of the second gait cycle between heel strike and toe-off with calibrated terrain model curves and the predicting further comprises providing by the management computing device the predicted type of upcoming terrain.

7. The method as set forth in claim 1 wherein the first gait sensor is positioned at a location on the second appendage of the subject so as to switch from a first reading indicating a first position in the gait cycle to second reading indicating a second position in the gait cycle once during the gait cycle to determine when a threshold value is exceeded.

8. The method as set forth in claim 4 wherein the second gait cycle is derived from the second terrain data.

9. The method as set forth in claim 1 wherein the first gait sensor and the first proximity sensor each comprise a proximity sensor.

10. The method as set forth in claim 9 wherein the proximity sensor comprises one of an infrared sensor, an ultrasonic sensor, and a laser sensor.

11. The method as set forth in claim 5 further comprising determining by the management computing device at least one of when the gait pattern of the subject has changed over time, average gait speed, changes in the gait speed, or one or more deviations from the gait pattern based on the second gait cycle, wherein the predicting further comprises providing by the management computing device the determined change in the gait pattern over time, the determined average gait speed, the determined changes in the gait speed, or the determined one or more deviations from the gait pattern.

12. The method as set forth in claim 1 wherein the first appendage comprises an orthotic or prosthesis and further comprising adapting the subject's foot position to the predicted upcoming terrain by actuating the orthotic or prosthesis in response to the signal.

13. A non-transitory computer readable medium having stored thereon instructions for simultaneously monitoring terrain and gait of a subject traversing terrain comprising machine executable code which when executed by at least one processor, causes the processor to perform steps comprising:
    characterizing a gait pattern of the subject traversing a plurality of terrain types for each of the plurality of terrain types traversed by:
    receiving by a management computing device a first terrain data from a first proximity sensor on a first appendage of the subject, comprising determining a distance between the first proximity sensor and a surface of an approaching terrain throughout a gait cycle of the subject while traversing each of the plurality of terrain types and receiving by the management computing device a first gait speed data relating to the gait of the subject from a first gait sensor on a second appendage of the subject throughout the gait cycle of the subject while traversing each of the plurality of terrain types to establish a periodic terrain model normalized by gait period by applying a periodic function to the first terrain data establishing gait speed as an independent variable to the periodic terrain model specific to the subject for each of the plurality of terrain types traversed, wherein the first and second appendages can be the same or different appendages;

monitoring the gait pattern of the subject traversing a second terrain by receiving by the management computing device a second terrain data from the first proximity sensor and a second gait speed data from a second gait sensor to scale in time the periodic terrain model normalized by gait period to the incoming second gait speed data to identify the second terrain being traversed from established periodic terrain models;

predicting an upcoming terrain by the management computing device from the received second gait speed data and the second terrain data for the subject; and providing a signal to the subject or device based on the predicted upcoming terrain.

14. The non-transitory computer readable medium as set forth in claim 13 wherein the first proximity sensor and the first gait sensor are the same sensor.

15. The non-transitory computer readable medium as set forth in claim 13 wherein the first proximity sensor and the first gait sensor comprise at least two separate sensors.

16. The non-transitory computer readable medium as set forth in claim 13 further comprising defining a second gait cycle for the subject by the management computing device based on the second gait speed data and the predicting further comprises providing by the management computing device the second gait cycle.

17. The non-transitory computer readable medium as set forth in claim 16 further comprising identifying a type of terrain by the management computing device based on comparing the received second terrain data and the second gait cycle with calibrated terrain curves and the providing further comprises predicting by the management computing device the identified type of terrain traversed.

18. The non-transitory computer readable medium as set forth in claim 17 further comprising predicting a type of upcoming terrain by the management computing device based on comparing the received second terrain data and the second gait cycle over a portion of the second gait cycle between heel strike and toe-off with calibrated terrain curves and the providing further comprises predicting by the management computing device the predicted type of upcoming terrain.

19. The non-transitory computer readable medium as set forth in claim 13 wherein the first gait sensor is positioned at a location on the second appendage of the subject so as to switch from a first reading indicating a first position in the gait cycle to second reading indicating a second position in the gait cycle once during the gait cycle to determine when a threshold value is exceeded.

20. The non-transitory computer readable medium as set forth in claim 16 wherein the second gait cycle is derived from the second terrain data.

21. The non-transitory computer readable medium as set forth in claim 13 wherein the first gait sensor and the first proximity sensor each comprise a proximity sensor.

22. The non-transitory computer readable medium as set forth in claim 21 wherein the proximity sensor comprises one of an infrared sensor, an ultrasonic sensor, and a laser sensor.

23. The non-transitory computer readable medium as set forth in claim 17 further comprising determining by the management computing device at least one of when the gait pattern of the subject has changed over time, average gait speed, changes in the gait speed, or one or more deviations from the gait pattern based on the second gait cycle, wherein the predicting further comprises providing by the management computing device the determined change in the gait pattern over time, the determined average gait speed, the determined changes in the gait speed, or the determined one or more deviations from the gait pattern.

24. The non-transitory computer readable medium as set forth in claim 13 wherein the first appendage comprises an orthotic or prosthesis and further comprising adapting the subject's foot position to the predicted upcoming terrain by actuating the orthotic or prosthesis in response to the signal.

25. A terrain and gait monitoring system comprising:
one or more sensors; and
a management computing device coupled to the one or more sensors, the management computing device comprising a memory coupled to one or more processors which are configured to execute programmed instructions stored in the memory comprising:
characterizing the gait pattern of the subject traversing a plurality of terrain types for each of the plurality of terrain types traversed by:
receiving first terrain data from a first proximity sensor on a first appendage of the subject, comprising determining a distance between the first proximity sensor and a surface of an approaching terrain throughout a gait cycle of the subject while traversing the each of the plurality of terrain types;
receiving a first gait speed data relating to the gait of the subject from a first gait sensor on a second appendage of the subject throughout the gait cycle of the subject while traversing each of the plurality of terrain types to establish a periodic terrain model normalized by gait period by applying a periodic function series to the first terrain data establishing gait speed as an independent variable to the periodic terrain model specific to the subject for each of the plurality of terrain types traversed, wherein the first and second appendages can be the same or different appendages;
monitoring the gait pattern of the subject traversing a second terrain by receiving by the management computing device a second terrain data from the first proximity sensor and a second gait speed data from a second gait sensor to scale in time the periodic terrain model normalized by gait period to the incoming second gait speed data to identify the second terrain being traversed from established periodic terrain models;
predicting an upcoming terrain from the received second gait speed data and the second terrain data for the subject; and
providing a signal to the subject or device based on the predicted upcoming terrain.

26. The system as set forth in claim 25 wherein the first proximity sensor and the first gait sensor are the same sensor.

27. The system as set forth in claim 25 wherein the first proximity sensor and the first gait sensor comprise at least two separate sensors.

28. The system as set forth in claim 25 further comprising defining a second gait cycle for the subject by the management computing device based on the second gait speed data and the predicting further comprises providing by the management computing device the second gait cycle.

29. The system as set forth in claim 28 further comprising identifying a type of terrain by the management computing device based on comparing the received second terrain data and the second gait cycle with calibrated terrain curves and the providing further comprises predicting by the management computing device the identified type of terrain traversed.

30. The system as set forth in claim 29 further comprising predicting a type of upcoming terrain by the management computing device based on comparing the received second terrain data and the second gait cycle over a portion of the second gait cycle between heel strike and toe-off with calibrated terrain model curves and the predicting further comprises providing by the management computing device the predicted type of upcoming terrain.

31. The system as set forth in claim 25 wherein the first gait sensor is positioned at a location on the second appendage of the subject so as to switch from a first reading indicating a first position in the gait cycle to second reading indicating a second position in the gait cycle once during the gait cycle to determine when a threshold value is exceeded.

32. The system as set forth in claim 28 wherein the second gait cycle is derived from the second terrain data.

33. The system as set forth in claim 25 wherein the first gait sensor and the first proximity sensor each comprise a proximity sensor.

34. The system as set forth in claim 33 wherein the proximity sensor comprises one of an infrared sensor, an ultrasonic sensor, and a laser sensor.

35. The system as set forth in claim 29 further comprising determining by the management computing device at least one of when a gait pattern of the subject has changed over time, average gait speed, changes in the gait speed, or one or more deviations from the gait pattern based on the defined gait cycle, wherein the predicting further comprises providing by the management computing device the determined change in the gait pattern over time, the determined average gait speed, the determined changes in the gait speed, or the determined one or more deviations from the gait pattern.

36. The system as set forth in claim 25 wherein the first appendage comprises an orthotic or prosthesis and further comprising adapting the subject's foot position to the predicted upcoming terrain by actuating the orthotic or prosthesis in response to the signal.

* * * * *